(12) United States Patent
Konduri et al.

(10) Patent No.: US 8,137,796 B2
(45) Date of Patent: Mar. 20, 2012

(54) REUSABLE MATERIAL FOR COLLECTING SAMPLES FOR ANALYSIS

(75) Inventors: Ravi K. Konduri, Heathrow, FL (US); Neil Alan Stewart, Orlando, FL (US); Edward E. A. Bromberg, Orlando, FL (US); Yarelis M. Rios, Orlando, FL (US); David H. Fine, Cocoa Beach, FL (US); John M. Oelschlaeger, Palm Harbor, FL (US); Mark Fraser, Nashua, NH (US)

(73) Assignee: L-3 Communications CyTerra Corporation, Orlando, FL (US)

( * ) Notice: Subject to any disclaimer, the term of this patent is extended or adjusted under 35 U.S.C. 154(b) by 768 days.

(21) Appl. No.: 12/188,843

(22) Filed: Aug. 8, 2008

(65) Prior Publication Data

US 2009/0038418 A1    Feb. 12, 2009

Related U.S. Application Data

(60) Provisional application No. 60/955,123, filed on Aug. 10, 2007.

(51) Int. Cl.
*G01N 1/04* (2006.01)
*G01N 1/08* (2006.01)

(52) U.S. Cl. .................. 428/221; 73/864.71; 428/141

(58) Field of Classification Search ............... 73/864.71; 428/141, 221
See application file for complete search history.

(56) References Cited

U.S. PATENT DOCUMENTS

| 5,741,984 A | 4/1998 | Danylewych-May et al. |
| 2004/0232052 A1 | 11/2004 | Call et al. |
| 2005/0048859 A1 | 3/2005 | Canham et al. |
| 2007/0034024 A1 | 2/2007 | Syage |
| 2007/0044579 A1* | 3/2007 | Yamaguchi et al. ......... 73/865.5 |
| 2011/0129644 A1* | 6/2011 | Rule et al. .................... 428/141 |

OTHER PUBLICATIONS

International Search Report and Written Opinion for corresponding International Application No. PCT/US2008/072652, mailed Nov. 5, 2008, 11 pages.

* cited by examiner

*Primary Examiner* — Thomas P Noland
(74) *Attorney, Agent, or Firm* — Fish & Richardson P.C.

(57) ABSTRACT

A particle-harvesting material includes a flexible, reusable, and thermally conductive material including a rough surface having dimples of a size within a first range of sizes, a microstructure including interstices of a second range of sizes, the second range of sizes including sizes smaller than the first range of sizes, and an etched portion on the rough surface configured to attract particles upon contact between the particles and the etched portion.

27 Claims, 11 Drawing Sheets

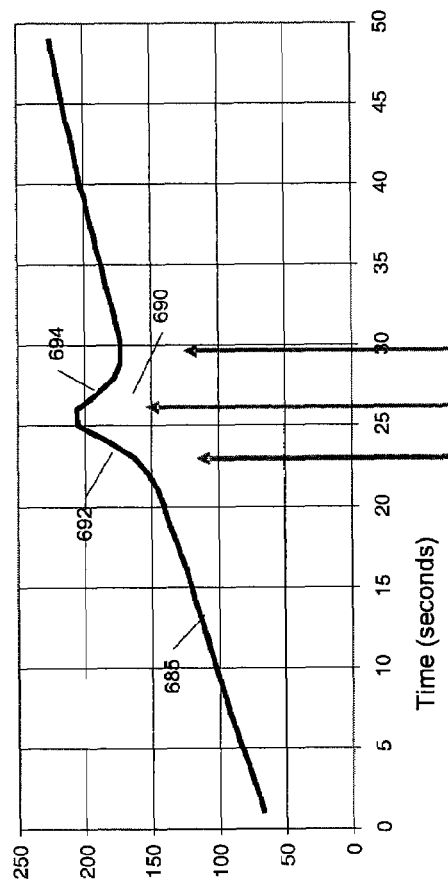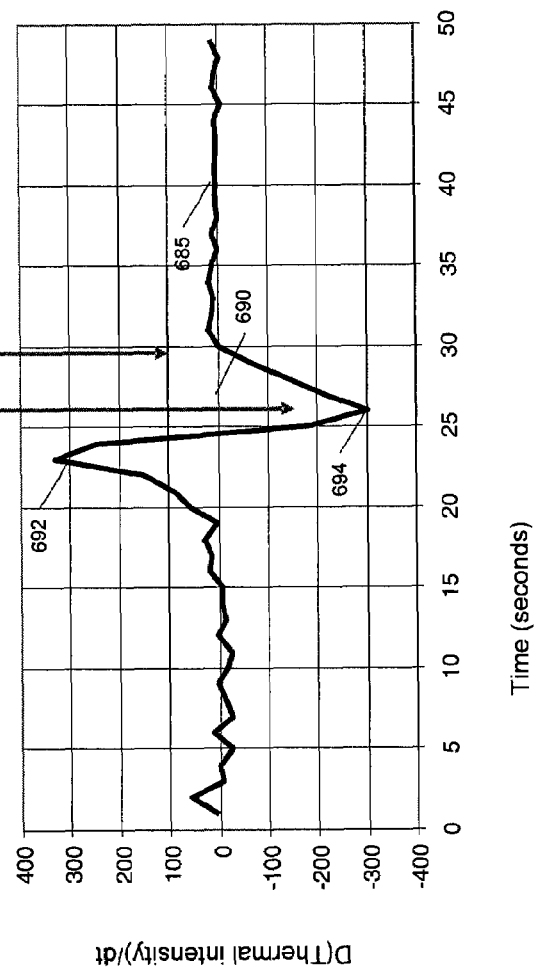

REUSABLE MATERIAL FOR COLLECTING SAMPLES FOR ANALYSIS

CROSS-REFERENCE TO RELATED APPLICATION

This application claims priority to U.S. Provisional Application Ser. No. 60/955,123, titled HIGH EFFICIENCY WIPES FOR HARVESTING EXPLOSIVE RESIDUES, and filed on Aug. 10, 2007, which is incorporated by reference in its entirety.

TECHNICAL FIELD

This description relates to a material for collecting samples for analysis.

BACKGROUND

Materials for collecting samples of residues may be made of relatively thin and insubstantial materials that are not generally designed for repeated use.

SUMMARY

In one general aspect, a particle-harvesting material includes a flexible, reusable, and thermally conductive material including a rough surface having dimples of a size within a first range of sizes, a microstructure including interstices of a second range of sizes, the second range of sizes including sizes smaller than the first range of sizes, and an etched portion on the rough surface configured to attract particles upon contact between the particles and the etched portion.

Implementations may include one or more of the following features. The particles may include crystalline particles of energetic materials. The particles may include particles of varying sizes and the particles may be retained in the dimples of the material and in the interstices of the microstructure. The etched portion on the rough surface may include an etched portion configured to attract particles through an electromagnetic force. The etched portion may include an etched portion configured to attract particles by physical contact between the particles and the etched portion. The particle-harvesting material may include a catalytic material coating the conductive material.

The thermally conductive material may include a metallic mesh. A polymer coating may be included on a second surface of the thermally conductive material and on one or more edges of the thermally conductive material. A rigid strip may be included along one or more edges of the thermally conductive material. The thermally conductive material may be electrically conductive. The thermally conductive material may have uniform thermal and electrical conductivity. The rough surface having dimples may include a surface having scratches. The thermally conductive material may include a material able to withstand application of radiation having a temperature sufficient to initiate thermal decomposition of an energetic material. The microstructure may be within the thermally conductive material and may extend to at least one surface of the thermally conductive material.

In another general aspect, a rough surface is created on a durable, thermally conductive material, the rough surface including dimples having a first range of sizes. A portion of the rough surface is etched to create a microstructure within the thermally conductive material, the microstructure including interstices having a second range of sizes, the second range of sizes including sizes smaller than the first range of sizes. A second material is incorporated into the thermally conductive material such that the thermally conductive material has uniform thermal conductivity, and the thermally conductive material is placed into a frame sized to fit into an explosives-detection apparatus.

Implementations may include one or more of the following features. The thermally conductive material may be coated with a polymer material. The thermally conductive material may be coated with a catalyst material. Creating a rough surface on a durable, thermally conductive material, the rough surface including dimples having a first range of sizes may include applying an abrasive material to a surface of the thermally conductive material. The thermally conducting material may include a mesh, and incorporating a second material into the thermally conductive material may include filling openings in the mesh with the second material. Etching a portion of the rough surface may include placing the thermally conductive material into an etching solution, and placing the thermally conductive material into the etching solution may impart flexibility to the thermally conductive material.

In another general aspect, a cartridge includes a material configured to attract and retain particles. The material includes a rough surface having dimples within a first range of sizes, a microstructure including interstices of a second range of sizes, the second range of sizes including sizes smaller than the first range of sizes, and an etched portion on the rough surface configured to attract particles upon contact between the particles and the etched portion. The cartridge also includes a frame surrounding the material, the frame being sized to fit into a material-detection apparatus that accepts the frame.

In another general aspect, a kit includes a particle-harvesting material and a frame, where the particle-harvesting material is configured to attract and retain particles. The material includes a rough surface having dimples within a first range of sizes, a microstructure including interstices of a second range of sizes, the second range of sizes including sizes smaller than the first range of sizes, and an etched portion on the rough surface configured to attract particles upon contact between the particles and the etched portion. The frame is configured to surround the particle-harvesting material.

Implementations may include one or more of the following features. The frame may be configured to be received by a detection apparatus. The frame may fit into the detection apparatus in only one orientation. The frame may include a rigid material that supports the material, and the frame surrounds edges the particle-harvesting material.

Implementations of any of the techniques described above may include a method, a process, a system, a device, an apparatus, a kit, a cartridge, or instructions stored on a computer-readable medium. The details of one or more implementations are set forth in the accompanying drawings and the description below. Other features will be apparent from the description and drawings, and from the claims.

DESCRIPTION OF THE DRAWINGS

FIGS. 6C-6F show illustrations of thermal signature data.

DETAILED DESCRIPTION

Figure 1:
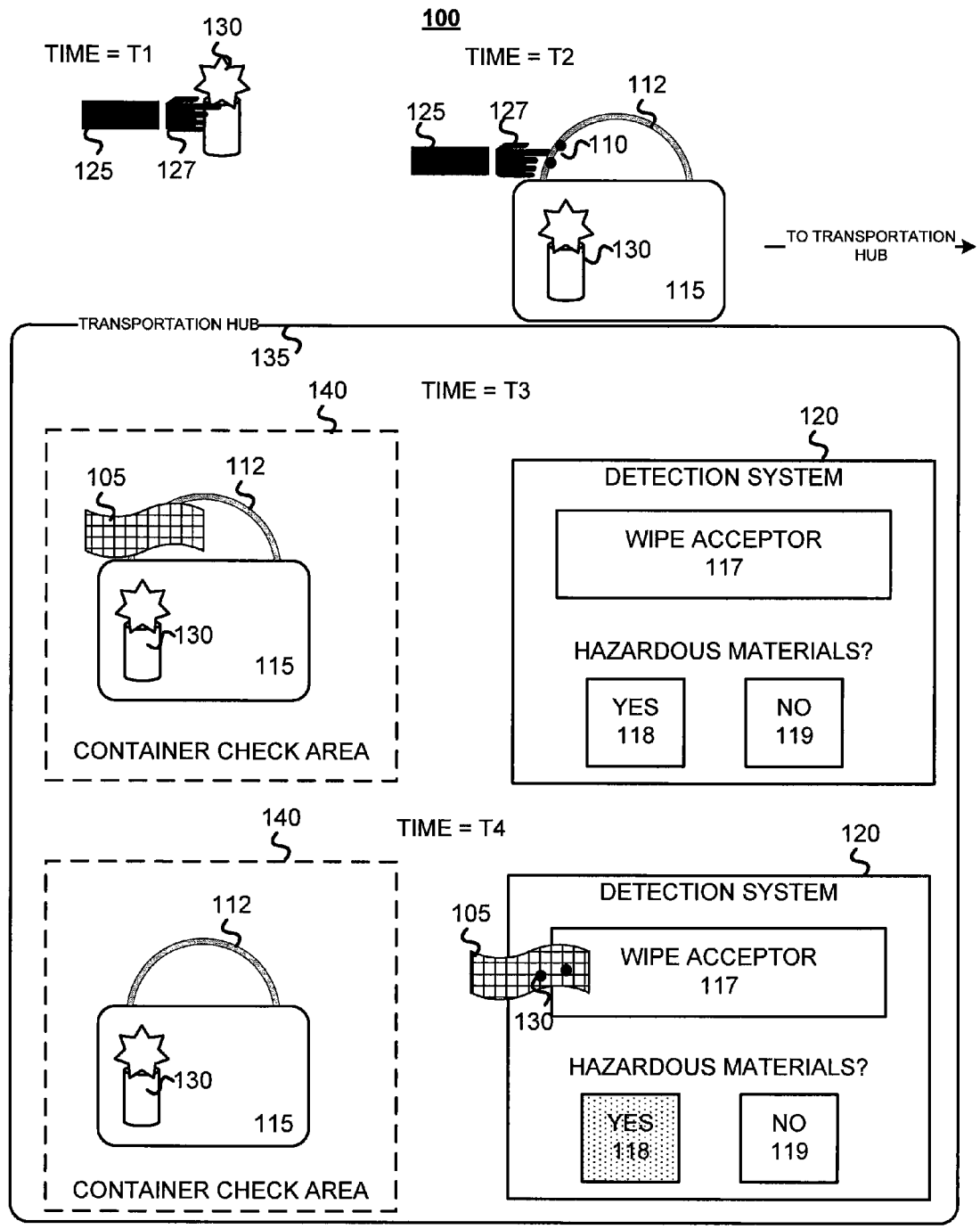
FIG. 1 illustrates an example scenario in which a particle-harvesting material contacts a handle of a suitcase.

Referring to FIG. 1, an example scenario 100 illustrates a durable and reusable particle-harvesting material 105 that is used to extract and retain particles 110 from a surface of an object upon contact between the particle-harvesting material 105 and the surface of the object. As discussed in more detail below, for example, with respect to FIG. 2A, the particle-harvesting material 105 is made by tailoring the physical, chemical, thermal, and electrical properties of a base material into a particle-harvesting material 105 that is optimized to extract and retain particles having certain characteristics (such as size and shape) upon contact with the particles and that may be reused hundreds of times without noticeable degradation in performance. The extracted particles also may be referred to as samples or sample residues.

In the example shown in FIG. 1, a small amount of explosive residue (e.g., 100 micrograms) is present on a handle 112 of a suitcase 115. The presence of the explosive residue on the handle 112 may indicate that the suitcase 115 includes an explosive or that a person carrying the suitcase 112 is carrying explosives. Thus, detection of the presence of the residue on the handle 112 may provide an indication of a possible security threat. To check for the presence of such particles on the handle 112, an operator of a detection system 120 places the particle-harvesting material 105 in contact with the handle 112 of a suitcase 115 to extract the particles 110 from the handle 112. The structure of the particle-harvesting material 105 allows the particles 110 to be retained in the particle-harvesting material 105. After extracting the particles 110 from the surface of the handle 112, the operator of the detection system 120 inserts the particle-harvesting material 105 into a wipe acceptor 117 of the detection system 120. The detection system 120 determines whether the particle-harvesting material 105 includes particles of a material of interest. In the example shown in FIG. 1, the detection system 120 includes indicators 118 and 119 that indicate whether the particle-harvesting material 105 includes particles of one or more materials of interest.

The materials of interest may include hazardous and/or contraband materials such as exothermic compounds, narcotics, controlled substances, biological agents, hazardous chemicals, chemical and/or biological warfare agents, and materials that may be made into hazardous and/or contraband material when combined with other materials. Exothermic compounds may include military-grade explosives, commercial explosives, and homemade explosives that are made up, at least partially, of crystalline particles. In some implementations, the particle-harvesting material 105 may collect and retain liquids and/or vapors of materials of interest in addition to, or instead of, particles of materials of interest.

Persons who handle explosives, controlled substances, narcotics, or other materials of interest tend to become contaminated with trace residues of the materials. For example, in the scenario 100 shown in FIG. 1, a person 125 grasps a bomb 130 made of explosive materials at a time "t1" with a hand 127. The explosive materials included in the bomb 130 include crystalline particles, and other trace residues, that are transferred from the bomb 130 to the hand 127 and remain on the hand 127 even after the person 125 releases the bomb 130. Thus, when the person 125 touches other objects, such as clothing, luggage, and packages with the hand 127, the crystalline particles and other trace residues are transferred from the hand 127 to the object. The particles and other trace residues may remain on the hand 127 even after the hand 127 is washed or the hand 127 is rubbed with, for example, a towel or on clothing.

In the example scenario shown in FIG. 1, the person 125 releases the bomb 130 from the grasp of the hand 127 and places the bomb 130 into the suitcase 115. At a time "t2," the person 125 touches the hand 127 to the handle 112 of the suitcase 115, and by touching the hand 127 to the handle 112, crystalline particles and other trace residue of the explosives in the bomb 130 are transferred to the handle 112.

The suitcase 115 is then transported to a transportation hub 135 that screens persons and packages for hazardous materials by swabbing a surface of the persons and packages with the particle-harvesting material 105 and analyzing the particle-harvesting material 105 with the detection system 120. The transportation hub 135 may be, for example, an civilian or military airport, a train station, or a bus terminal in which the detection system 120 is located. Although, in the example scenario shown in FIG. 1, the detection system 120 is located in the transportation hub 135, in other examples the detection system 120 may be located in another location in which containers, persons, and/or individual items are screened for the presence of items of interest. For example, the detection system 120 may be located in a venue where groups of persons congregate, such as a public building, a sports arena, or a concert hall or in a venue where official business is conducted, such as a courthouse or government administration building.

The detection system 120 analyzes the particle-harvesting material 105 after the particle-harvesting material 105 is used to swab an object. If the surface of object has particles of a material of interest, the particle-harvesting material extracts the particles, and the detection system 120 determines that the object, or a person carrying the object, may pose a threat.

The particle-harvesting material 105 is a thermally conductive material that is modified from a base material into a material suitable for attracting, extracting, and retaining particles of materials of interest. Extraction of the particles 110 from a surface of an object, such as the handle 112 of the suitcase 115 may be effected by the chemical composition of the surface on which the particles 110 reside (which also may be referred to as a substrate), chemical interactions between the substrate and the particles 110 that determine how firmly the particles 110 are held by the substrate, the roughness of the substrate and the particle-harvesting material 105, and the flexibility of the substrate and the particle-harvesting material 105. By tailoring the thermal, electrical, and chemical properties of the particle-harvesting material 105 and the surface roughness of the particle-harvesting material 105, the particle-harvesting material 105 may be modified to optimize the ability of the particle-harvesting material 105 to extract and retain particles in a range of sizes known to be associated with particles of materials of interest. For example, the particle-harvesting material 105 may be used as part of a security system deployed in an airport that screens persons and baggage by detecting residues of explosives on the surface carry-on baggage and personal effects. The explosives may be composed of crystalline particles having a size of one to two hundred µm, and the particle-harvesting material 105 may be tailored to collect particles of one to two hundred microns.

Continuing with the example scenario of FIG. 1, at a time "t3," the suitcase 115 arrives in a container check area 140 located at the transportation hub 135. Even though time has passed between the time "t2" when the hand 127 touched the handle 112 of the suitcase 115, crystalline particles from the bomb 130 are still present on the handle 112. The amount of time that the particles from the bomb 130 remain on the handle varies depending on the type of material from which the handle 112 is made and the volatility of the explosive material included in the bomb 130. For example, some plastic explosives may include plasticizers that make the particles stick more readily to the handle 112, and such particles may remain on the handle 112 for months. Particles of volatile compounds may remain on the handle 112 for less than one hour. However, particles of most explosives remain on the handle 112 even after attempts to remove the particles from the handle 112.

At time "t3," the particle-harvesting material 105 comes into contact with the handle 112. Contact between the particle-harvesting material 105 and the handle 112 may occur, for example, when an operator of the detection system 120 contacts the particle-harvesting material 105 to the handle 112. As discussed in more detail with respect to FIG. 2C, a frame that is sized to fit into the wipe acceptor 117 may surround the particle-harvesting material 105.

At a time "t4," the particle-harvesting material 105 includes particles 110, which were extracted by the particle-harvesting material 105 by contacting the particle-harvesting material 105 to the contaminated handle 112. The particle-harvesting material 105 is placed into the detection system 120 and analyzed to determine whether the particles 110 include particles that originated from a material of interest. In the example shown in FIG. 1, the particles 110 are crystalline particles that originated from the bomb 130, and, thus, the detection system 120 presents an indication that a material of interest is present on the handle 112 of the suitcase 115.

Figure 2A:
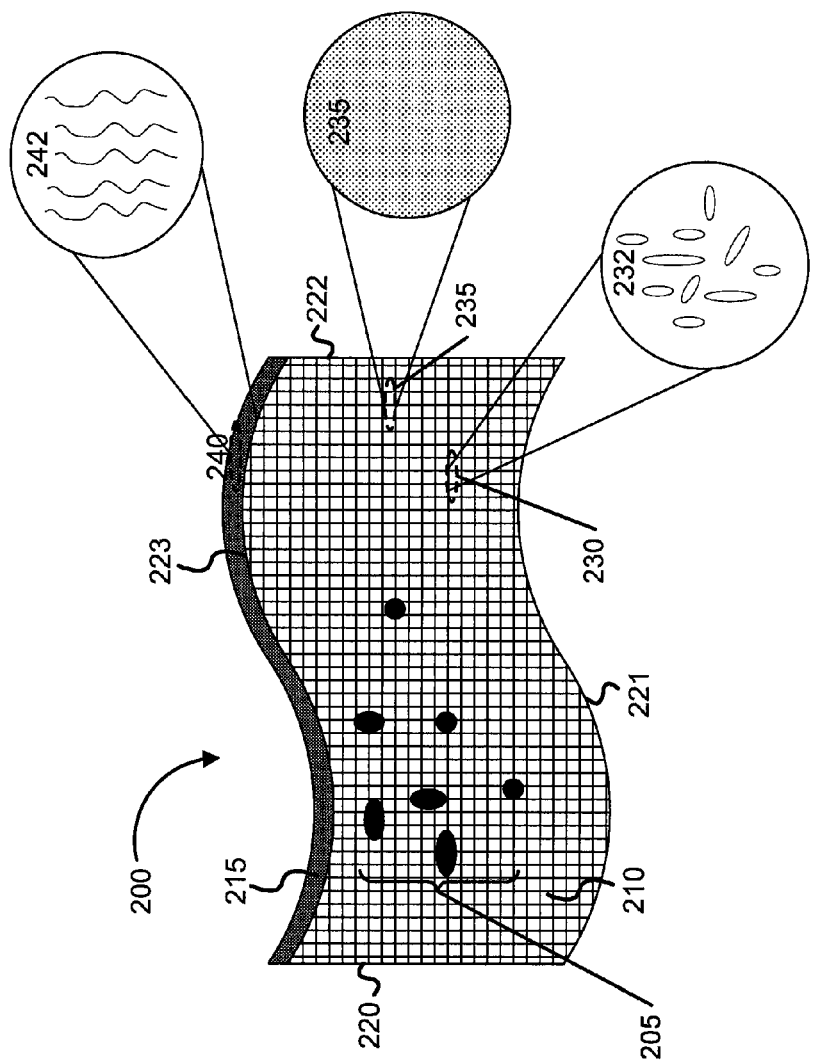
FIG. 2A shows an example of a particle-harvesting material.

Referring to FIG. 2A, an example of a particle-harvesting material 200 that attracts, extracts, and retains particles 205 from an object is shown. The particle-harvesting material 200 may be similar to the particle-harvesting material 105 discussed above with respect to FIG. 1. The particle-harvesting material 200 includes a top surface 210, and the particle-harvesting material 200 has a thickness 215 and edges 220-223. In the example shown in FIG. 2A, the top surface 210 is shown, however, the particle-harvesting material 200 also has a second, or bottom, surface (not shown) that opposes the surface 210. The particle-harvesting material 200 also includes a rough portion 230 on the surface 210, an etched portion 235 on the surface 210, and a microstructure 240 that is formed within the particle-harvesting material 200.

The particle-harvesting material 200 may be made from a thermally conductive material (which may be referred to as the base material) such as a metallic mesh, a solid metallic material, or a carbon weave, that, unmodified, would not necessarily attract and retain the particles 205. The base material is a material that is durable, thus the particle-harvesting material 200 may be used multiple times (e.g., tens or hundreds of times) to extract, retain, and analyze particles without replacement or substantial degradation in performance of the particle-harvesting material 200. Additionally, in some implementations, the particle-harvesting material 200 is heated to a temperature sufficient to initiate thermal decomposition of an explosive material and monitored in order to determine whether the particle-harvesting material 200 includes particles of an explosive material. Thus, the base material is also a material that is able to withstand repeated application of a high temperature. The particle-harvesting material 200 may be, for example, a metal mesh, such as a SS 316 stainless steel mesh, SS316L mesh (which is a low-carbon stainless steel mesh), an Inconel® (available from Special Metals Corporation of New York) mesh, a Nichrome® (available from Driver-Harris Wire Company of New Jersey), a foil material, a solid metal sheet, or a carbon weave.

The top surface 210 of the base material that forms the particle-harvesting material 200 may be smooth initially, and the rough portion 230 that covers all or part of the top surface 210 is formed, for example, by physically contacting the surface 210 with a roughening material such as abrasive paper and/or a brush having abrasive bristles. The rough portion 230 acts to loosen, or extract, particles from a substrate (such as the handle 112 of the suitcase 115). The contact between the roughening material and the surface 210 creates dimples, or scratches, 232, which retain particles that are of a size similar to the dimples 232. Thus, the rough portion 230 and the dimples 232 within the rough portion 230 act to loosen particles from the substrate and help to retain particles within the particle-harvesting material 200 for subsequent analysis of the particles 205.

The dimples 232 may be uniform in size or the dimples 232 may have a distribution of sizes and shapes selected to match the distribution of sizes and shapes of the particles to be collected by the particle-harvesting material 200. For example, the dimples 232 may be a mix of scratch-like depressions on the surface 210 that have approximately straight edges, circular depressions on the surface 210, and elliptical depressions on the surface 210. The sizes of the dimples 232 may be expressed as, for example, a diameter of the longest axis of a cross-section of a dimple, and the dimples 232 may have a range of sizes from approximately one µm to two hundred µm in an application in which the particle-harvesting material 200 collects crystalline particles of common explosives. The distribution of the sizes and shapes of the dimples 232 is determined by the mechanism used to create the dimples 232. Creation of the dimples 232 is discussed in more detail with respect to FIGS. 3 and 4A.

The particle-harvesting material 200 also includes the etched portion 235 and the microstructure 240. As discussed in more detail with respect to FIGS. 3 and 4B, the etched portion 235 may be created by exposing the particle-harvesting material 200, the surface 210, or a portion of the surface 210 to an etching solution. The etching solution may be an acid or a base. The etching solution may penetrate the surface 210 through all or part of the thickness 215 to create the etched portion 235 on the surface 210 and the microstructure 240 within the particle-harvesting material 200. The microstructure 240 may be completely beneath the surface 210 or the microstructure 240 may extend to the surface 210, the bottom surface (not shown), and/or one or more of the edges 220-223. Application of the etching solution also may impart flexibility and ductility to the particle-harvesting material 200, which may improve the ability of the particle-harvesting material 200 to collect the particles 205 (e.g., the flexibility may allow the particle-harvesting material 200 to conform to the shape of the substrate being sampled on contact, come into direct contact with a greater portion of the substrate being sampled, and thus collect more particles).

The etching solution may deposit ions or other charged particles and atoms on the etched portion 235, and the ions may help to attract the particles 205 to the particle-harvesting material 200. The particles 205 may be attracted to the particle-harvesting material 200 through physical contact between the etched portion 235 and the particles 205 and/or by an electromagnetic force (such as chemical bonding) between the etched portion 235 and the particles 205. The presence of the etched portion 235 may allow the particle-harvesting material 200 to attract particles that the particle-harvesting material 200 would otherwise not attract. For example, the particle-harvesting material 200 may be a solid metallic material such as foil that would not ordinarily bond with crystalline particles found in an explosive residue. However, the presence of the etched portion 235 allows the foil to attract the crystalline particles. For example, the etching solution may be hydrochloric acid that leaves chlorine ions on the etched portion 235. The chlorine ions may attract and bond to crystalline particles of explosive materials that may not be attracted by the metal foil alone. Thus, like the rough portion 230, the etched portion 235 may help to extract the particles 205 from a substrate (such as the handle 112 of the suitcase 115) and retain the particles 205 on the particle-harvesting material 200.

Application of the etching solution to the particle-harvesting material 200 also imparts a fine molecular structure within the particle-harvesting material 200 to create the microstructure 240. The microstructure may have interstices 242 (e.g., small gaps, openings, and/or pitting within and on the internal surfaces of the particle-harvesting material 200) throughout the microstructure 240, and the interstices 242 may have a range of sizes, some of which may be smaller than the smallest dimple of the dimples 232. For example, the dimples 232 may have a range of sizes between one and two hundred µm and the interstices 242 may have sizes between a few nanometers nm to ten µm. Because the interstices 242 may have a different size range than the dimples 232, the interstices 242 may help to retain particles having different sizes than the particles retained by the dimples 232. Thus, the presence of both the dimples 232 and the interstices 242 may expand the range of sizes of particles that the particle-harvesting material 205 may extract and hold. Although, in the discussion above, the etched portion 235 is created by exposing the surface 210 to the etching solution, the etched portion 235 may be made by other techniques, such as exposing the surface 210 to a focused ion beam or by laser etching the surface 210. For example, laser etching may be used to impart a repeated pattern of scratches on the surface 210 and within the particle-harvesting material 200. In the example shown in FIG. 2A, the edges 220-223 are shown as curved to represent the flexibility of the particle-harvesting material 200. However, the particle-harvesting material may have straight edges in other examples.

Figure 2B:
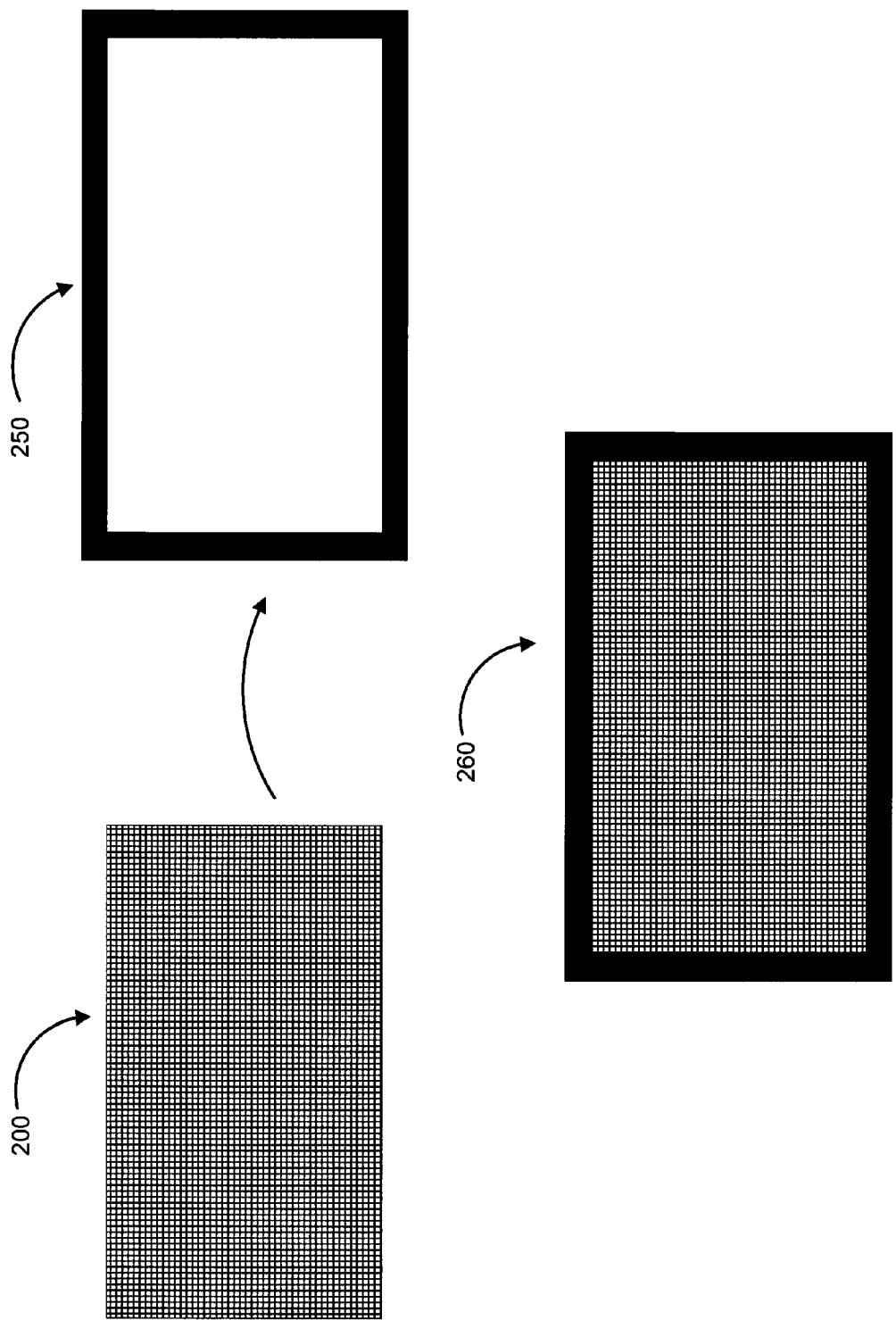
FIG. 2B shows an example of a particle-harvesting material and a frame for the particle-harvesting material.
Figure 2C:
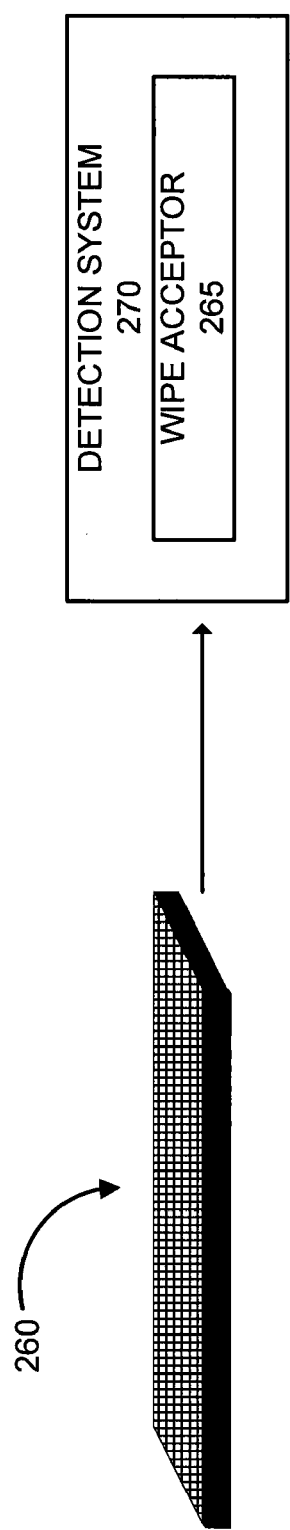
FIG. 2C shows an example of a sample wipe and a detection system.

Referring to FIGS. 2B-2C, the particle-harvesting material 200 is placed into a frame 250 to create a reusable sample wipe 260 that is configured to fit into a wipe acceptor 265 of a detection system 270. The reusable sample wipe 260 also may be referred to as a cartridge, trap, sample trap, swap, coupon, or swatch. The detection system 270 may be similar to the detection system 120 discussed above with respect to FIG. 1. The frame 250 may be a metallic material or a non-metallic material (e.g., a plastic) that surrounds the edges 220-223 of the particle-harvesting material 200. The frame 250 may be a rigid frame. In some implementations, the frame 250 may contact fewer than all of the edges 220-223. For example, the frame 250 may contact two opposing edges (e.g., edges 220 and 222 or edges 221 and 223) rather than all of the edges 220-223. The frame 250 provides strength and support to the particle-harvesting material 200 and, by holding the particle-harvesting material 200, helps to prevent damage to the particle-harvesting material 200 that would otherwise occur due to crumpling, wrinkling, or crinkling of the particle-harvesting material 200 during use (for example, while contacting the particle-harvesting material 200 to a substrate, transporting the particle-harvesting material 200, or inserting the particle-harvesting material 200 into the detection system 270), storage, and/or transport of the particle-harvesting material 200. Thus, the frame 250 may help to prolong the life of the particle-harvesting material 200.

The frame 250 may be configured such that the reusable sample wipe 260 may only fit into the wipe acceptor 265 in one direction. For example, the reusable sample wipe 260 may be keyed to a particular shape such that the sample wipe 260 only fits into the wipe acceptor 265 in the proper direction. This may ensure that an operator (which may be a human operator or an automated machine, such as a robotic arm) of the detection system 270 inserts the sample wipe in the direction that results in the best results. For example, the detection system 270 may be designed such that a sensor within the detection system is optimized to analyze and detect materials on the side of the sample wipe 260 that includes the surface 210. In this example, the frame 250 may be constructed such that the sample wipe 260 is accepted into the wipe accepted 265 only when the surface 210 is inserted face-up into the wipe acceptor 265.

In the example shown in FIGS. 2B and 2C, the frame 250 and the sample wipe 260 are rectangular. However, in other examples, the frame 250 and resulting sample wipe 260 may be other shapes, and the frame 250 and sample wipe 260 may be shaped to match the shape of the wipe acceptor 265. For example, the frame 250 and the sample wipe 260 may be square, circular, or elliptical. The frame 250 and the sample wipe 260 may be a five centimeter (cm) long and four (cm) wide rectangle having a thickness of three millimeters. The wipe acceptor 265 may be sized to be slightly larger than the sample wipe 260 such that the sample wipe 260 fits seamlessly into the wipe acceptor 265.

Figure 3:
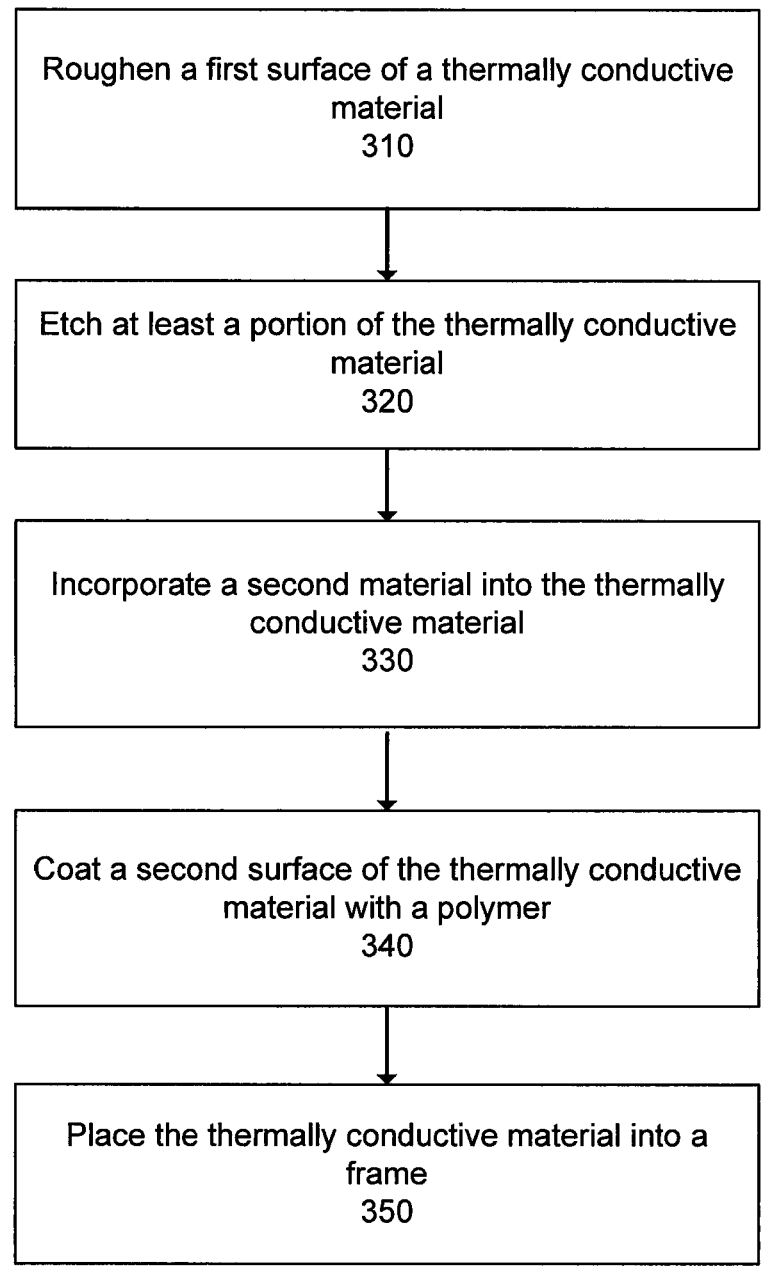
FIG. 3 shows an example process for making a particle-harvesting material.
Figure 4A:
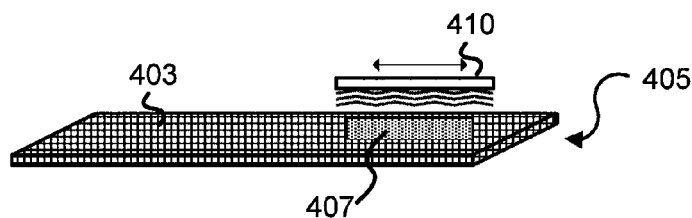
FIG. 4A illustrates a rough surface.

Referring to FIGS. 3 and 4, a sample process 300 may be used to create a sample wipe that attracts, extracts, and retains particles present on a substrate is illustrated. The sample wipe created by the process 300 may be similar to the sample wipe 260 discussed with respect to FIG. 2C. A first surface of a thermally conductive material is roughened (310). The thermally conductive material may be a solid material, such as a foil or a sheet of metal, or the thermally conductive material may be a mesh material that has a grid of openings formed between interwoven wires. The wires that make the mesh may be electrically conducting or semi-conducting. For example, the interwoven wires may be metallic or carbon. The thermally conductive material may include both electrically conductive and semi-conducting materials. The thermally conductive material may be a combination of a mesh material and a solid material. For example, the thermally conductive material may be a mesh in some portions and a solid material in other portions. The thermally conductive material is a durable material that may be reused (e.g., the thermally conductive material may be contacted to various substrates hundreds of times without noticeable physical degradation of the thermally conductive material). Additionally, the thermally conductive material is sufficiently flexible to conform to the shape of the surface of the substrate without cracking, breaking, or straining the thermally conductive material.

Referring also to FIG. 4, a first surface 403 of a thermally conductive material 405 may be roughened into a rough surface 407 by contacting the first surface 403 with an abrasive material 410. Contacting the abrasive material 410 to the first surface 403 mars the first surface 403 with scratches, depressions, dimples, pitting, or other types of physical abrasions. Contacting the abrasive material 410 to the first surface 403 may create dimples similar to the dimples 232 discussed above with respect to FIG. 2A. The abrasive material 410 may be, for example, sand paper (e.g., emery paper or aluminum oxide paper) or a brush having abrasive bristles. For example, the abrasive material 410 may be a brush that has nylon bristles that are infused with aggregate particles. The abrasive material 410 may be selected such that the rough surface 407 includes dimples that have a distribution of sizes and shapes that match the particles that the sample wipe is intended to collect and retain. For example, the grit of the abrasive material 410 may be selected such that the grit imparts scratches that have a distribution of depths, lengths, and widths that match the sizes of the particles to be collected.

The aggregate particles scratch the first surface 403 to create the rough surface 407. The abrasive material 410 may be applied to the first surface 403 by rubbing or brushing the first surface 403 with the abrasive material 410 with, for example, circular, translational, oscillatory, and/or random strokes. The application of the abrasive material 410 to the first surface 403 may be done manually or by an automated process. For example, the thermally conductive material 405 may be passed through automated scratching rollers. The abrasive material 410 is applied to the thermally conducting material 405 with a pressure sufficient to create the rough surface 407 but with less than that which would result in the abrasive material 410 rubbing through the thermally conductive material 405. The amount of pressure that is sufficient depends on the hardness and ductility of the thermally conducting material 405.

Although, in the example shown in FIG. 4, the abrasive material 410 is contacted to the first surface 403, in other examples, the abrasive material 410 may be contacted to another surface in addition to, or instead of, the first surface 403. For example, both the first surface 403 and a bottom surface (not shown) of the thermally conductive material 405 may be roughened with the abrasive material 410. In some implementations, the rough surface 407 may be created without the abrasive material 410. For example, the rough surface 407 may be pre-molded into the thermally conductive material 405 or created by pressing a material having a pattern of protrusions onto the first surface 403 of the conductive material 405.

Returning to FIG. 3, at least a portion of the thermally conductive material is etched (320). Etching the thermally conductive material results in an etched portion on a surface of the thermally conductive material and the formation of a microstructure within the thermally conductive material. The thermally conductive material may be etched with an acidic or basic etching solution. For example, the thermally conductive material may be etched with hydrochloric acid, iron chloride, or a mixture of chromic acid and nitric acid. The etched portion may be similar to the etched portion 235, and the microstructure may be similar to the microstructure 240, both of which are discussed above with respect to FIG. 2A. In particular, the etched surface may attract and bond particles of materials of interest, and the microstructure may help to retain the particles of interest.

Figure 4B:
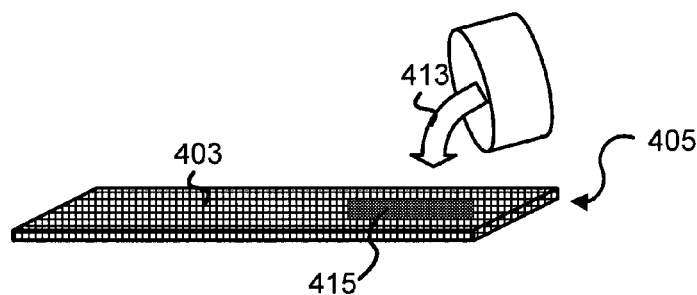
FIG. 4B illustrates an etching process.

Referring to also to FIG. 4B, an etching solution 413 may be poured onto the thermally conductive material 405 to create the etched surface 415. Although illustrated as a portion of the first surface 403, the etched surface 415 may cover the entire first surface 403 as well as edges and the bottom of the thermally conductive material 405. The example shown in FIG. 4B includes pouring the etching solution 413 onto the conductive material; however, in other examples, to etch the thermally conducting material, the thermally conductive material may be dipped into the etching solution 413 and/or placed into a bath of the etching solution 413.

The etching of the conductive material 405 may include using an electrically activated bath, which may result in the etching occurring more quickly as compared to not using the electrically activated bath. To etch the thermally conductive material 405 with an electrically activated bath, the thermally conductive material is placed into the etching solution and clamped into place, and an electric current is applied to pass through the etching solution for an amount of time that varies depending on the size of the thermally conductive material. For example, for a rectangular material that is about four (cm) by five (cm), the electric current may be applied for about two minutes. The thermally conductive material is removed from the bath and may be rinsed with water to conclude the etching process.

Referring to FIG. 3, a second material is incorporated into the thermally conductive material (330). The second material may be incorporated into the thermally conductive material in order to make the thermally conductive material heat uniformly. For example, the thermally conductive material may be a mesh material that includes air gaps between the wires or fibers that form the mesh. The air gaps have a different thermal conductivity than the wires, and the second material may be incorporated into the mesh material to completely close, partially close, or minimize, the air gaps and such that the mesh has a uniform, or nearly uniform, thermal conductivity. For example, the second material may be a metal, such as nickel, and the nickel may be incorporated into the mesh by electroplating, incorporation of nanoparticles of nickel into the mesh, or sintering pieces of nickel into the mesh. For example, nickel may be incorporated into the mesh through electrically activated or electroless deposition. Additionally, or alternatively, the second material may be incorporated into the mesh through infusion. For example, the mesh may be a polymer material, and the second material may be a carbon that is infused into the polymer mesh. The second material may be used to modify the thermally conductive material such that the thermally conductive material is uniformly electrically conductive. For example, incorporating a metallic material throughout the thermally conductive material may result in the thermally conductive material having a uniform electrical conductivity.

The thermally conductive material also may be coated, or otherwise treated, with a catalytic material. The thermally conductive material is used as part of a sample wipe (such as the sample wipe 260 discussed above with respect to FIGS. 2B and 2C), and the sample wipe may be placed in a detection system to analyze particles retained by the sample wipe. As discussed in more detail with respect to FIGS. 5 and 6A-6F, in some implementations, the detection system analyzes the sample wipe for the presence of particles of explosive materials by heating the sample wipe to a temperature sufficient to trigger an explosion of the particles. The detection system monitors a thermal signature of the sample wipe to determine if the thermal signature includes characteristics of a thermal signature known to be associated with explosives. By coating the thermally conductive material, which will be used as part of the sample wipe, with the catalyst, the explosion of the particles may occur more quickly and require less input energy. Thus, the presence of the catalyst may improve the performance of the detection system.

A second surface of the thermally conductive material is coated with a polymer (340). Referring again to FIG. 4C, the second surface may be a surface 409 that is opposite of the surface 403, such as a bottom surface. The second surface also may include edges of the thermally conductive material aside from the surface 403. Coating, or otherwise attaching or treating, the conductive material 405 with the polymer may ensure that static forces on the thermally conductive material 405 are maintained and not influenced by electric charges that may exist on the body of an operator who is using the thermally conductive material 405. The presence of the polymer also may allow the thermally conductive material to be used to collect and retain vapors, particles in a vapor, and/or liquids for further analysis. However, the thermally conductive material may collect and retain vapors even without the polymer. For example, metals that catalytically react with vapors may be incorporated into the thermally conductive material such that, when exposed to vapors, the thermally conductive material collects and retains the vapors. In a second example, cooling the thermally conductive material and exposing the cooled thermally conductive material to vapor may cause the vapor to condense on the thermally conductive material such that the properties of the vapor may be analyzed by analyzing the collected vapor.

The polymer may be any polymer that withstands a temperature sufficient to initiate a thermal decomposition of particles of explosive materials. For example, the polymer may by a polymide or Teflon® (available from E. I. DuPont de Nemours and Company of Delaware). To coat the thermally conductive material with the polymer, the thermally conductive material may, for example, be dipped into liquefied polymer material and the material allowed to dry to form a flexible and solidified polymer on the thermally conductive material. Alternatively, the liquefied polymer material may be brushed or poured onto the thermally conductive material.

Figure 4C:
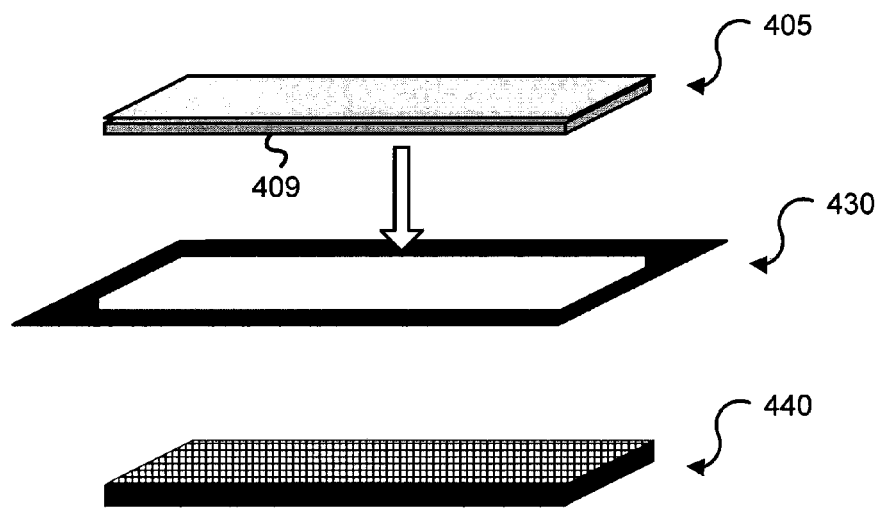
FIG. 4C illustrates placing a particle-harvesting material into a frame.

Returning to FIG. 3, the thermally conductive material is placed in a frame (350). The frame may be a frame similar to the frame 250 discussed above with respect to FIG. 2B. Referring also to FIG. 4C, an example of placing the thermally conductive material 405 into a frame 430 to form a sample wipe 460 is illustrated. In the illustration of FIG. 4C, the thermally conductive material 405 is shown as being incorporated with the second material and having a polymer coating on a bottom surface 409. Placing the thermally conductive material 405 into the frame 430 may provide strength and stability to the thermally conductive material 405, and also may improve the usable life and the ease of usability of the thermally conductive material 405. In addition, strips of a rigid material may be placed along one or more edges of the thermally conductive material 405. The strips may reinforce and strengthen a portion of the conductive material 405 that contacts substrates, and the strips may further prolong the life of the thermally conductive material. For example, the strips may be along two opposite edges of the thermally conductive material.

The thermally conductive material 405 may be secured into the frame 430 by snapping the thermally conductive material 405 into place in the frame 430 such that the edges of the thermally conductive 405 material contact the frame 430. The thermally conductive material 405 may be secured to the frame 430 by gluing, taping, interference fit, or soldering. The thermally conductive material 405 may be removable from the frame 430 or permanently attached to the frame 430. The thermally conductive material 405 may be placed in the frame 430 prior to distribution to the users, or the user may place the thermally conductive material 405 in the frame 430.

Figure 5:
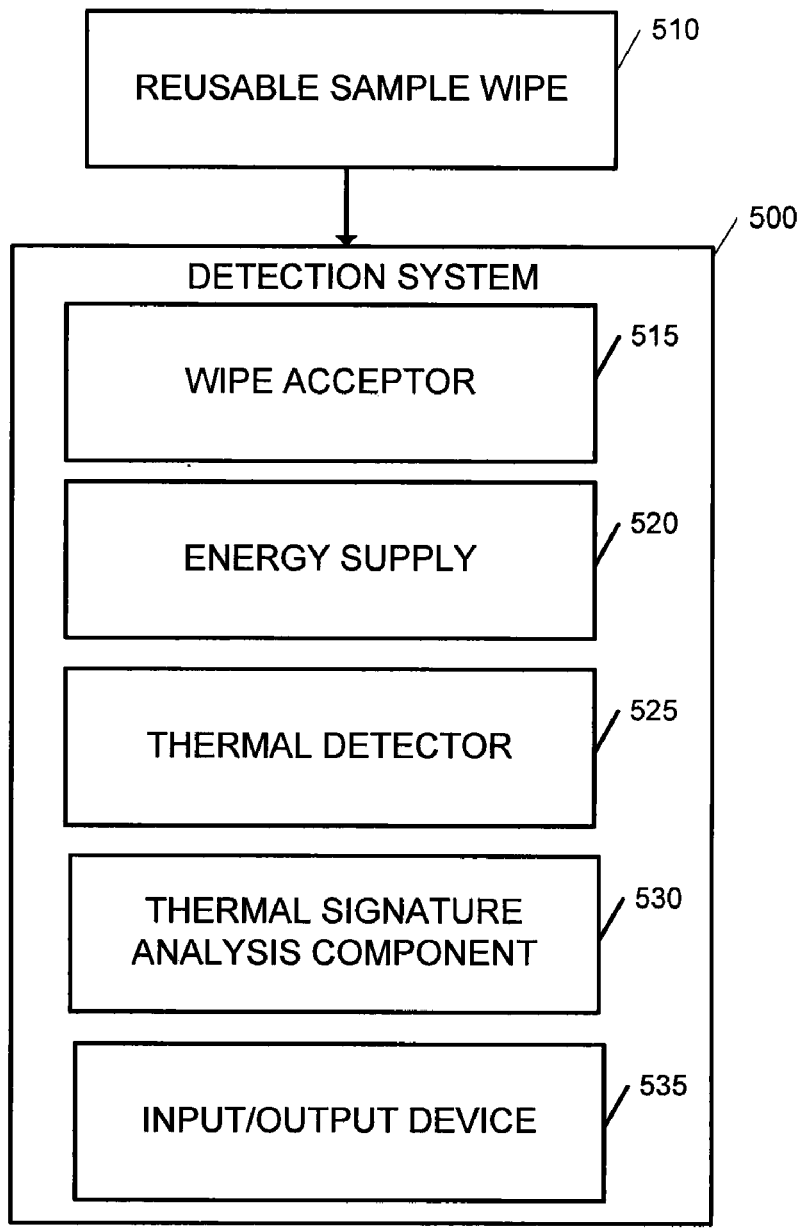
FIG. 5 shows an example of a detection system.

Referring to FIG. 5, an example detection system 500 may be used to determine whether explosives are present on a reusable sample wipe 510 by analyzing a thermal signature of the sample wipe 510 as the sample wipe is heated. The reusable sample wipe 510 may be similar to the sample wipe 260 or the sample wipe 460 discussed above with respect to FIG. 2C and FIG. 4C, respectively. The reusable sample wipe 510 may be similar to the thermally conductive material 200 (e.g., the reusable sample wipe 510 may be a thermally conductive material without a supporting frame).

When heated to the point of thermal decomposition, particles of explosive materials release and absorb energy in a characteristic manner that may be used to determine whether the particles are particles of explosive material. The detection system 500 heats the sample wipe to a temperature sufficient to initiate thermal decomposition of explosive particles on the sample wipe. Although the detection system 500 analyzes the sample wipe 510 for the presence of particles of explosive materials, the sample wipe 510 may be used in a variety of material detection systems that are designed to analyze particles extracted and retained by the sample wipe 510. For example, the sample wipe 510 such as systems designed to analyze particles extracted and retained by the sample wipe to determine whether particles of narcotics, controlled substances, materials that may be used to make explosives and incendiary devices when combined with other materials, or other hazardous materials are present on the sample wipe 510. The presence of such particles on the sample wipe 510 indicates that a substrate contacted with the sample wipe 510 may have been handled by a person carrying hazardous materials. Additionally, the sample wipe 510 may be used in detection systems that analyze the sample wipe 510 for the presence of liquids or vapors.

The detection system 500 includes a wipe acceptor 515, an energy supply 520, a thermal detector 525, a thermal signature analysis component 530, an input/output device 535, a processor 540, and electronic storage 545.

The wipe acceptor 515 may be a slot, cavity, tray, carousel, or other type of receptacle that is configured to accept and hold the sample wipe 510. The energy supply 520 supplies energy to the sample wipe 510 held in the wipe acceptor 515 and to any explosive particles present on the sample wipe 510. For example, the energy supply 520 may supply sufficient activation energy to initiate thermal decomposition (e.g., an explosion) of particles present on the sample wipe 510. The energy supply may heat the sample wipe 510 to, for example, 300° C. in less than one second. The sample wipe 510 may be a thermally conductive material that is not electrically conductive, or a thermally conductive material that is semi-electrically conductive, and the energy supply may be a flash lamp, or other source of radiant heat, that heats the sample wipe 510 and any particles included in or on the sample wipe 510. The sample wipe 510 may be an electrically conductive material, and the energy supply 520 may supply an electric current to the sample wipe 510 to resistively heat the sample wipe 510.

The detection system 500 also includes the thermal detector 525, which may be, for example, an infrared detector that detects radiant energy released from any particles on the sample wipe 510. The thermal detector 525 may generate video or image data of the sample wipe 510 while the sample wipe 510 is heated by the detection system 500. The thermal detector 525 may be one or more infrared detectors sensitive to radiation having wavelengths in the short-wave infrared (SWIR) spectral band (3 to 5 microns), the mid-wave infrared (MWIR) spectral band (5 to 8 microns), or long-wave infrared (LWIR) spectral band (8 to 12 microns). In some implementations, the thermal detector 525 may convert the detected radiant energy into temperature based on a predetermined calibration. The detection system 500 also includes a thermal signature analysis component 530, which may analyze the data from the detector 525 to determine whether explosives are present on the sample wipe 510. For example, the analysis 630 discussed below with respect to FIG. 6A may be implemented with the thermal signature analysis component 530. The thermal signature analysis component 530 includes an electronic memory configured to store instructions that, when executed, implement an analysis such as the analysis 630. The thermal signature analysis component 530 also includes a processor and a storage device.

The detection system 500 also includes an input and output device 535. The input and output device 535 may include a printer, a touchscreen for selecting commands for the system 500, and/or any other type of input/output device for communicating with and receiving data from the system 500.

Figure 6A:
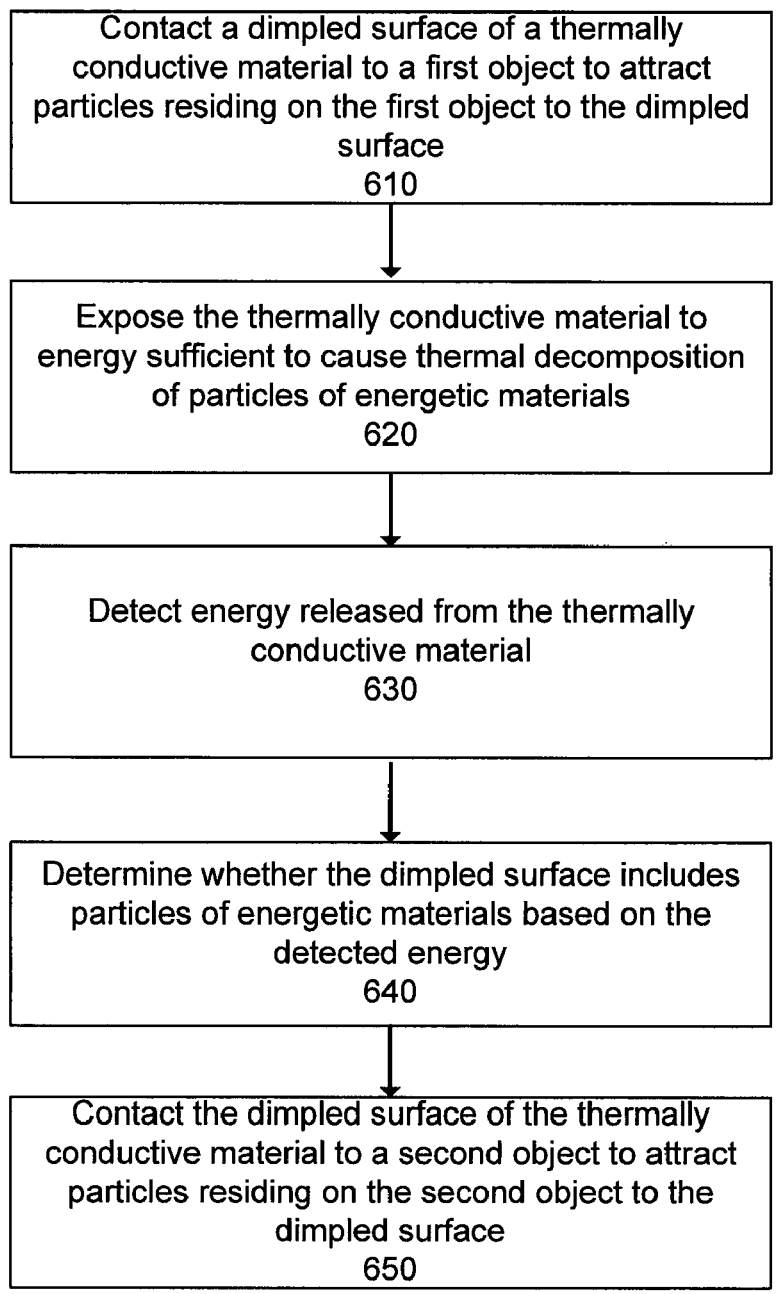
FIGS. 6A and 6B show an example process for determining the presence of materials of interest.
Figure 6B:
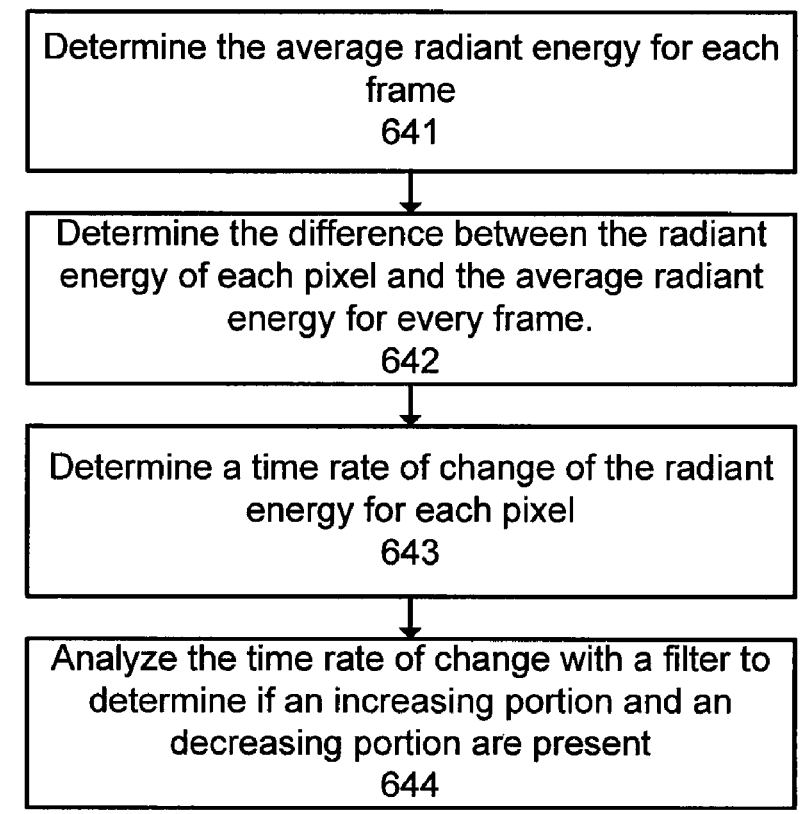

Referring to FIG. 6A, an example process 600 for determining whether a sample wipe includes particles of energetic materials (such as explosive materials) is shown. In particular, the process 600 analyzes energy released from the sample wipe 510 as the sample wipe 510 is heated in the system 500 to determine whether the sample wipe 510 includes particles of energetic materials. Additionally, because of the durability of the sample wipe 510, the process 600 may be repeated hundreds of times without replacing the sample wipe 510 and without experiencing a noticeable degradation in performance.

A dimpled surface of a thermally conductive material is brought into contact with a first object (610). Contacting the thermally conductive material to the first object may attract particles residing on a surface of the first object to the thermally conductive material. The thermally conductive material may be a sample wipe such as the sample wipes 260, 460, and 510 discussed above, and the dimpled surface may be a rough surface such as the rough surface 230 discussed with respect to FIG. 2A. The first object may be, for example, a surface of a suitcase, knapsack, cardboard box, or item of clothing worn by a person passing through an airport security checkpoint.

The thermally conductive material is exposed to energy sufficient to cause thermal decomposition (e.g., explosion) of particles of energetic materials (620). Exposing the thermally conductive material to energy may include placing the thermally conductive material into a detection system such as the detection system 500 discussed with respect to FIG. 5 and heating the thermally conductive material. For example, the thermally conductive material may be placed into the wipe acceptor 515 and heated with the energy supply 520. The thermally conductive material and any particles included in the thermally conductive material release energy as the thermally conductive material is heated. The released energy is detected (630). The released energy may be detected by a sensor such as the thermal detector 525 discussed above with respect to FIG. 5.

Whether the dimpled surface includes particles of energetic materials is determined based on the detected energy (640). In more detail and referring also to FIG. 6B, a time-dependent thermal signature collected by the thermal detector 525 is analyzed to determine whether the sample wipe 510 includes particles of an energetic material. Whether a possible energetic material is present is determined based on analysis of a time-dependent thermal signature generated from data collected by a detector array used to monitor a thermal energy status of the sample wipe 510, and any particles included in or on the sample wipe 510, are heated. The detector array may be, for example, the detector 525 discussed above, and the detector array may be a long-wave or mid-wave infrared detector. The detector 525 may be an array and/or the detector 525 may include additional detectors sensitive to energy of other wavelengths. The thermal energy status of the sample area may be the radiant energy released from or absorbed by the sample wipe 510 and/or it may be the temperature of the sample wipe 510. In general, the heat released from the sample wipe 510 as the sample wipe 510 is heated may be detected by the detector 525 as radiant energy. The detected radiant energy may be used to determine a time-dependent thermal signature of the sample wipe 510. In some implementations, the detected radiant energy may be converted to a corresponding temperature. In this implementation, the time-dependent thermal signature is based on the temperature of the sample wipe 510 as the sample area is heated over time.

As discussed in more detail below, analysis of the time-dependent thermal signature for characteristics of an explosion may allow a determination of whether the sample wipe 510 includes possible energetic materials. For example, supplying an explosive material with sufficient energy causes the material to explode. When the explosion occurs, heat is released from the explosion into the surrounding environment. This heat release may be referred to as an exotherm, and the exotherm is characterized by a rapid increase in the radiant energy released from the sample wipe 510. The explosive material is consumed during the explosion. After the explosive material is consumed, the explosion ends, and the sample area cools to the surrounding temperature. This cooling is characterized by a decrease in the radiant energy released from the sample area as compared to the radiant energy released at the peak of the exotherm.

Thus, time-dependent thermal signatures of explosives include an exotherm that includes a rapid rise in radiant energy to a peak radiant energy over a first time interval followed by a decrease in radiant energy from the peak radiation energy over a second time interval. Because time-dependent thermal signatures of materials other than explosives generally do not include such an exotherm, the presence of an exotherm in a time-dependent thermal signature indicates that the thermal signature was created by heating an energetic material. Thus, analyzing thermal signatures for the presence of an exotherm allows a determination of whether possible energetic materials are present without comparing the thermal signature to signatures included in a predefined library of thermal signatures.

The process 640 analyzes the radiant energy released over time from the sample area to determine if the sample area includes a possible energetic material. As discussed above, the radiant energy of a sample area is monitored using, for example, an infrared camera or a detector such as the detector 525. The process 630 may be performed by one or more processors included in the thermal signature analysis component 530 and/or the detection system 500 discussed above with respect to FIG. 5.

Figure 6D:
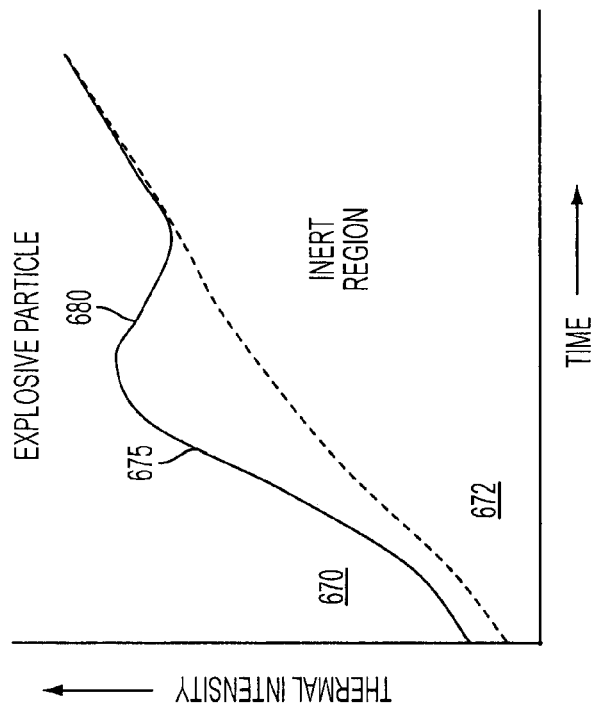
Figure 6C:
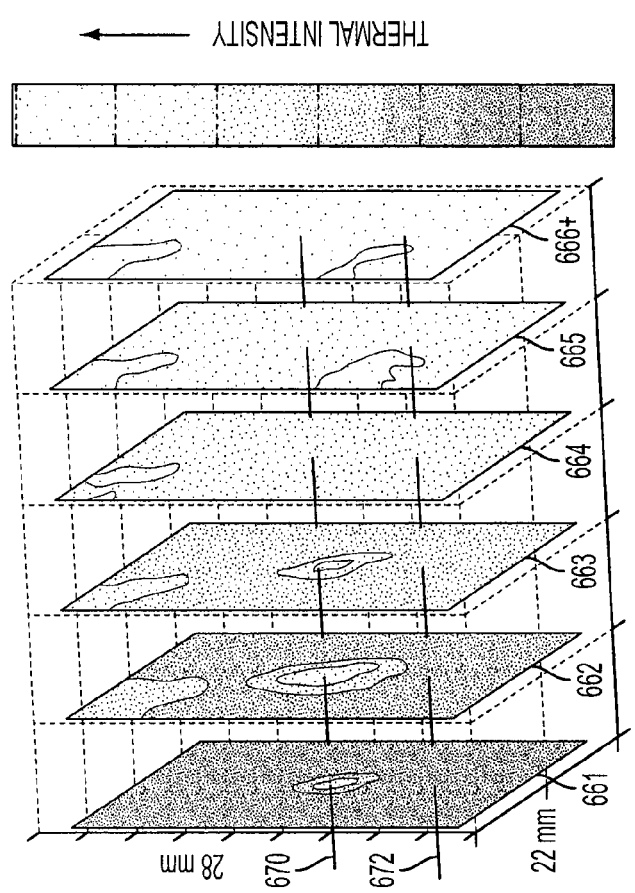

Referring to FIG. 6C, an illustration of thermal signature data is shown. For example, such data may be used to determine whether the sample wipe 510 includes particles of an explosive material. In the example shown in FIG. 4C, data is collected using, for example, an infrared sensor (which may be the detector 525) by taking snapshots, or frames, (such as snapshots 661, 662, 663, 664, 665, and 666) of the samples at various times. In this example, the collected data shows the heat released from the samples as a function of time.

In the example shown in FIG. 6C, the infrared sensor that includes an array of 320×240 pixels monitors a sample area that is 28 millimeters tall and 22 millimeters wide. The frames may be collected at regular intervals. For example, the frames may be collected at a rate of 60 frames per minute such that one frame is collected every 16.7 milliseconds. The example shown in FIG. 6C includes six frames, however more or fewer frames may be collected. For example, the frames may be collected for two seconds.

The frames are analyzed to determine a time-dependent thermal signature of each pixel, and the thermal signature is used to determine whether possible energetic materials are present. The frames 661, 662, 663, 664, 665, and 666 image the sample area and include a target region 670 and an inert region 672. In the example shown in FIG. 6C, the target region 670 includes explosive materials and the inert region 672 does not. The inert region 672 also may be referred to as the background or the surrounding region. As seen in FIG. 6C, as heat is applied to the sample area, the amount of heat released from the target region 670 is different from that released from the inert region 672.

Referring again to FIG. 6B, the average radiant energy is determined for each frame (621). For example, the value of each pixel in each of the frames 661, 662, 663, 664, 665, and 666 may represent the radiant energy released by the region of the sample area imaged by the pixel. Thus, the average value of the pixels in the frame 661 represents the average radiant energy released by the sample area at the time when frame 661 was collected. In another example, each pixel in each of the frames 661, 662, 663, 664, 665, and 666 may be converted from radiant energy to temperature. In this example, the average of the values of the pixels in the frame represents the average temperature of the sample area.

The difference between the radiant energy at each pixel and the average value is determined for each pixel in each frame (622). Thus, the average value for a particular frame determined in (621) is subtracted from the value of each pixel in that frame. Accordingly, the thermal energy status (e.g., the radiant energy or temperature) as a function of time may be determined for each pixel. Referring to FIG. 6D, an illustration of thermal signature data is shown. In the illustration, an example of the radiant energy of the pixel 670 and the pixel 672 as a function of time are shown. In this example, the pixel 672 images a portion of the sample area that does not include energetic materials, and the pixel 670 images a portion of the sample are that includes explosive material. As compared to the pixel 672, the radiant energy of the pixel 670 increases at time 675 as the energetic materials the pixel images are heated and explode and the radiant energy of the pixel 670 decreases at time 680 as the explosion consumes the energetic material and the area that the pixel 670 is imaging cools to the surrounding temperature.

Referring to FIG. 6B again, a time rate of change (e.g., a derivative with respect to time) is determined for each pixel (623). The time rate of change may be the time rate of change of the radiant energy or the temperature. FIGS. 6E and 6F show an illustration of thermal signature data. In the illustration, an example of the radiant energy and the time rate of change of the radiant energy detected by a pixel that images energetic materials, such as the pixel 670, and a pixel that images a region without energetic materials, such as the pixel 672, respectively. In particular, FIG. 6E is an illustration of thermal intensity versus time for a pixel 685 that images a region that includes explosive material and a pixel 690 that images a region without explosive material. FIG. 6F is an illustration of a derivative with respect to time for the radiant energy detected by the pixels 685 and 690. The time rate of change of the pixel 685 may be determined by comparing the value of the pixel 685 in one with the value of the same pixel in a previously or subsequently collected frame. The time rate of change may be determined in any manner that a derivative may be determined. For example, the comparison may be a subtraction, and the resulting value is generally divided by the time that elapsed between collection of the frames. In general, the comparison is performed between the same pixel in two different frames after the average value for each frame is subtracted. However, in some implementations, the comparison may be done without subtracting the average value from the frames.

Accordingly, the time rate of change for each pixel is determined. The time rate of change may be the time rate of change of the radiant energy detected by that pixel or the time rate of change of the temperature of the region of the sample area the pixel is imaging. The time rate of change for each pixel may be the time-dependent thermal signature of the region of the sample area that is imaged by the pixel. In other implementations, the time-dependent thermal signature may be the radiant energy of the pixels over time. In still other implementations, the time-dependent thermal signature may be the temperature of each pixel over time.

Referring to FIG. 6E, the time rate of change of the pixel 685 includes an increasing portion 692 and a decreasing portion 694. The increasing portion 692 and the decreasing portion 694 are also apparent in the data shown in FIG. 6F. The presence of the increasing portion 692 and the decreasing portion 694 may indicate that an explosive is present. Additionally, the width of the portion of the thermal intensity versus time that includes the increasing portion 692 and the decreasing portion 694 may provide an additional indication of the presence of explosive materials. For example, the exotherm of an explosive material occurs more rapidly than the exotherm of a material that is merely flammable but not explosive. Thus, the width of the portion of the thermal intensity versus time that includes the increasing portion 692 and the decreasing portion 694 is more narrow (e.g., occurs over a shorter amount of time) for an explosive material. In the example shown in FIGS. 6E and 6F, the width is approximately ten seconds, however, in other examples, the width may be much less (e.g., tens of microseconds).

Referring again to FIG. 6B, the time rate of change (e.g., time-dependent thermal signature) determined for each pixel in (623) is analyzed by a filter to determine whether an increasing portion and a decreasing portion are present in the time-dependent thermal signature (624). Based on whether an an increasing portion and a decreasing portion are present, the presence of a possible energetic material may be determined. Other techniques may be used to determine whether the sample includes possible energetic materials. For example, the spectral signature data may be used to determine whether the sample includes possible energetic materials.

Referring again to FIG. 6A, the dimpled surface of the thermally conductive material is contacted to a second object (650). Any particles that may have been collected when the thermally conductive material was contacted to the first object are no longer in or on the thermally conductive material due to the heating of the thermally conductive material discussed above. The heating is sufficient to decompose particles and remove the particles from the surface of the thermally conductive material. However, some oxidized residues may remain on the thermally conductive material, but these oxidized materials do not interfere with the detection of particles collected in subsequent applications of the thermally conductive material to substrates. Contacting the dimpled surface of the thermally conductive material to the second object attracts particles residing on the second object to the dimpled surface. The second object may be different from the first object. For example, the first object and the second object may be two pieces of luggage in a checked-baggage screening area. The second and first object may be the same object. For example, a suitcase may be flagged for further screening and contacted with the thermally conductive material a second time. In addition to contacting the second object, the dimpled surface of the thermally conductive material may be reused to contact hundreds or thousands of objects without replacing the thermally conductive material or portions of the thermally conductive material and without noticeable degradation in the performance of the thermally conductive material.

It is understood that other modifications are within the scope of the claims. For example, the detection system 500 may be a detection system configured to determine whether the sample wipe 510 includes particles of a narcotic material, or determine whether the sample wipe 510 includes liquid explosives.

What is claimed is:

1. A particle-harvesting material, comprising:
   a flexible, reusable, and thermally conductive material configured to extract a particle from a second material when contacted to a surface of the second material, the thermally conductive material including a rough surface having dimples of a size within a first range of sizes, the first range of sizes including a size substantially similar to a diameter of the particle;
   a microstructure including interstices of a second range of sizes, the second range of sizes including sizes smaller than the first range of sizes; and
   an etched portion on the rough surface.

2. The particle-harvesting material of claim 1, wherein the particles are crystalline particles of energetic materials.

3. The particle-harvesting material of claim 1, wherein the particles comprise particles of varying sizes and the particles are retained in the dimples of the thermally conductive material and in the interstices of the microstructure.

4. The particle-harvesting material of claim 1, wherein the etched portion on the rough surface is configured to attract particles upon contact between the particles and the etched portion, and the etched surface comprises an etched portion configured to attract particles through an electromagnetic force.

5. The particle-harvesting material of claim 1, wherein the etched portion on the rough surface is configured to attract particles by physical contact between the particles and the etched portion.

6. The particle-harvesting material of claim 1 further comprising a catalytic material coating the conductive material, the catalytic material configured to increase the speed of a chemical decomposition of the particles that occurs in response to heating the thermally conductive material.

7. The particle-harvesting material of claim 1, wherein the thermally conductive material comprises a metallic mesh.

8. The particle-harvesting material of claim 1 further comprising a polymer coating on a second surface of the thermally conductive material and on one or more edges of the thermally conductive material.

9. The particle-harvesting material of claim 1 further comprising a rigid strip along one or more edges of the thermally conductive material.

10. The particle-harvesting material of claim 1, wherein the thermally conductive material is electrically conductive.

11. The particle-harvesting material of claim 10, wherein the thermally conductive material has uniform thermal and electrical conductivity.

12. The particle-harvesting material of claim 10, wherein the thermally and electrically conductive material comprises nickel.

13. The particle-harvesting material of claim 12, wherein the nickel covers an air gap in the thermally and electrically conductive material.

14. The particle-harvesting material of claim 1, wherein the rough surface having dimples comprises a surface having scratches.

15. The particle-harvesting material of claim 1, wherein the thermally conductive material comprises a material able to withstand application of radiation having a temperature sufficient to initiate thermal decomposition of an energetic material.

16. The particle-harvesting material of claim 1, wherein the microstructure is within the thermally conductive material and extends to at least one surface of the thermally conductive material.

17. The particle-harvesting material of claim 1, wherein the first range of sizes comprises sizes up to 10 microns.

18. The particle-harvesting material of claim 1, wherein the first range of sizes comprises sizes up to about 200 microns, and the second range of sizes comprises sizes up to about 10 microns.

19. The particle-harvesting material of claim 1, wherein the flexible, thermally conductive material is conformable to a shape associated with a surface of the second material.

20. The particle-harvesting material of claim 1, wherein the thermally conductive material is further configured to retain the extracted particle.

21. A cartridge comprising:
   a particle-harvesting material configured to attract and retain particles, the particle-harvesting material comprising:
      a flexible, reusable, and thermally conductive material configured to extract a particle from a second material when contacted to a surface of the second material, the thermally conductive material including a rough surface having dimples of a size within a first range of sizes, the first range of sizes including a size substantially similar to a diameter of the particle,
      a microstructure including interstices of a second range of sizes, the second range of sizes including sizes smaller than the first range of sizes, and
      an etched portion on the rough surface; and
   a frame surrounding the particle-harvesting material, the frame being sized to fit into a material-detection apparatus that accepts the frame.

22. A kit comprising a particle-harvesting material and a frame, wherein:
   the particle-harvesting material is configured to attract and retain particles, the particle-harvesting material comprising:
      a flexible, reusable, and thermally conductive material configured to extract a particle from a second material when contacted to a surface of the second material, the thermally conductive material including a rough surface having dimples of a size within a first range of sizes, the first range of sizes including a size substantially similar to a diameter of the particle,
      a microstructure including interstices of a second range of sizes, the second range of sizes including sizes smaller than the first range of sizes, and an etched portion on the rough surface; and the frame is configured to surround the particle-harvesting material.

23. The kit of claim 22, wherein the frame is further configured to be received by a detection apparatus.

24. The kit of claim 22, wherein the frame fits into the detection apparatus in only one orientation.

25. The kit of claim 22, wherein the frame comprises a rigid material that supports the material, and the frame surrounds edges the particle-harvesting material.

26. A particle-harvesting material, comprising:

a flexible, reusable, and thermally conductive material configured to extract an object held by a first surface from the first surface by making direct contact between the thermally conductive material and the first surface, the thermally conductive material including a rough surface having dimples of a size within a first range of sizes, the first range of sizes including a size substantially similar to a sample of the object; and an etched portion on the rough surface configured to attract a sample of the object upon contact between the object held by the first surface and the etched portion.

27. The particle-harvesting material of claim 26, wherein the object comprises a liquid explosive.

\* \* \* \* \*

UNITED STATES PATENT AND TRADEMARK OFFICE
CERTIFICATE OF CORRECTION

| | | |
|---|---|---|
| PATENT NO. | : 8,137,796 B2 | Page 1 of 1 |
| APPLICATION NO. | : 12/188843 | |
| DATED | : March 20, 2012 | |
| INVENTOR(S) | : Ravi K. Konduri et al. | |

It is certified that error appears in the above-identified patent and that said Letters Patent is hereby corrected as shown below:

In column 19, line 11, in Claim 25, after "edges" insert -- of --.

Signed and Sealed this
Twelfth Day of June, 2012

David J. Kappos
*Director of the United States Patent and Trademark Office*